United States Patent [19]

Sakai et al.

[11] Patent Number: 5,856,386
[45] Date of Patent: *Jan. 5, 1999

[54] PROCESS FOR CRYSTAL NUCLEATION OF CRYSTALLINE THERMOPLASTIC RESIN

[75] Inventors: Hideki Sakai; Mikio Nakagawa; Tetsuji Kasai, all of Waki-cho; Kimio Ueda, Osaka; Masao Maeda, Osaka; Yukiharu Yamada, Osaka; Hiroyuki Hori; Junji Tan, both of Waki-cho; Kan Matsumoto, Osaka, all of Japan

[73] Assignees: Mitsui Petrochemicals Industries, Ltd., Tokyo; Arakawa Chemical Industries, Ltd., Osaka, both of Japan

[*] Notice: This patent issued on a continued prosecution application filed under 37 CFR 1.53(d), and is subject to the twenty year patent term provisions of 35 U.S.C. 154(a)(2).

[21] Appl. No.: 786,250

[22] Filed: Jan. 22, 1997

Related U.S. Application Data

[62] Division of Ser. No. 463,676, Jun. 5, 1995, abandoned.

[30] Foreign Application Priority Data

| Jun. 9, 1994 | [JP] | Japan | 6-127478 |
| Jun. 9, 1994 | [JP] | Japan | 6-127479 |
| Aug. 23, 1994 | [JP] | Japan | 6-198758 |
| Aug. 23, 1994 | [JP] | Japan | 6-198759 |
| Aug. 23, 1994 | [JP] | Japan | 6-198760 |
| Aug. 23, 1994 | [JP] | Japan | 6-198761 |
| Apr. 5, 1995 | [JP] | Japan | 7-080361 |
| Apr. 5, 1995 | [JP] | Japan | 7-080362 |

[51] Int. Cl.[6] .................................................. C08L 93/04
[52] U.S. Cl. .......................... 524/271; 524/270; 524/274; 524/285
[58] Field of Search .................................. 524/270, 271, 524/272, 274, 285

[56] References Cited

U.S. PATENT DOCUMENTS

| 3,567,487 | 3/1971 | Poppe et al. ........................ 524/274 X |
| 3,598,776 | 8/1971 | Schirmer ................................ 524/274 |
| 3,663,488 | 5/1972 | Kail ........................................ 524/274 |
| 3,697,465 | 10/1972 | Joyner et al. .......................... 524/271 |
| 3,758,451 | 9/1973 | Weymann .......................... 524/274 X |
| 3,965,060 | 6/1976 | Lakshmanan .......................... 524/271 |
| 4,067,938 | 1/1978 | Jack ................................... 524/274 X |
| 4,127,546 | 11/1978 | Lundberg et al. ...................... 524/274 |
| 4,248,770 | 2/1981 | Matsuo et al. ..................... 524/270 X |
| 4,302,371 | 11/1981 | Matsuo et al. .......................... 524/272 |
| 4,340,514 | 7/1982 | Housel ............................... 524/273 X |
| 4,518,733 | 5/1985 | Ishikawa et al. ...................... 524/274 |
| 4,528,312 | 7/1985 | Edwards ............................. 524/271 X |
| 4,731,401 | 3/1988 | Moteki et al. ......................... 524/271 |
| 4,859,730 | 8/1989 | Lozachmeur .......................... 524/274 |
| 4,992,500 | 2/1991 | Klauck et al. ..................... 524/271 X |
| 5,021,492 | 6/1991 | Sandstrom et al. ................... 524/274 |
| 5,059,272 | 10/1991 | Kono et al. ........................ 524/270 X |
| 5,075,363 | 12/1991 | Tsuda et al. ....................... 524/284 X |
| 5,300,549 | 4/1994 | Ward et al. ............................. 524/321 |
| 5,308,395 | 5/1994 | Burditt et al. ..................... 524/270 X |
| 5,312,854 | 5/1994 | Wolf et al. ............................ 524/270 |
| 5,504,127 | 4/1996 | Wideman et al. ....................... 524/91 |

FOREIGN PATENT DOCUMENTS

| 00509370 | 6/1992 | European Pat. Off. ............... 524/270 |
| 0025846 | 2/1977 | Japan .................................... 524/274 |
| 58-160343 | 9/1983 | Japan . | |
| 63-139970 | 6/1988 | Japan . | |
| 1061366 | 3/1967 | United Kingdom ................... 524/274 |
| 1130019 | 10/1968 | United Kingdom ................... 524/270 |
| 9200354 | 1/1992 | WIPO ................................... 524/270 |

*Primary Examiner*—Judy M. Reddick
*Attorney, Agent, or Firm*—Sherman and Shalloway

[57] ABSTRACT

A crystalline thermoplastic resin composition comprises a rosin acid metallic salt and a crystalline thermoplastic resin. Optionally, a compatibilizing agent may also be included. The rosin acid metallic salt, which acts as a crystal nucleating agent, increases the crystallization rate of the crystalline thermoplastic resin and enables the formation of fine crystals of the resin. Thus, the crystalline thermoplastic resin composition can crystallize at a high rate, and provide molded articles having excellent mechanical properties and/or optical properties.

15 Claims, No Drawings

PROCESS FOR CRYSTAL NUCLEATION OF CRYSTALLINE THERMOPLASTIC RESIN

This application is a division of application Ser. No. 08/463,676, filed Jun. 5, 1995 now abandoned.

FIELD OF THE INVENTION

The present invention relates to the crystal nucleation of crystalline thermoplastic resins and a crystalline thermoplastic resin composition. More particularly, the invention relates to crystal nucleation to accelerate crystallization rates of crystalline thermoplastic resins and to a crystalline thermoplastic resin composition comprising a crystalline thermoplastic resin and a crystal nucleating agent.

BACKGROUND OF THE INVENTION

Because of their excellent properties such as processability, chemical resistance, electrical properties and mechanical properties, crystalline thermoplastic resins such as polyolefins, polyesters, polyamides and polyacetals have been processed into, for example, injection molded articles, hollow molded articles, films, sheets and fibers for various uses. However, these products do not always have sufficient rigidity, thermal rigidity or transparency for some uses.

It is known that the rigidity, thermal rigidity and transparency of the molded articles formed from the crystalline thermoplastic resins may be improved by the rapid formation of fine crystals in the molding process. Therefore, crystal nucleating agents such as talc have been conventionally used to accelerate crystallization rates of crystalline thermoplastic resins.

However, not all the conventional crystal nucleating agents, provide the resins with sufficient crystallization rates, and thus the resulting molded articles do not have always satisfactory mechanical properties such as rigidity and thermal rigidity and/or optical properties such as transparency and glossiness.

For example, JP-A 58-160343 discloses polyester compositions which comprise polyethylene terephthalate or polyester containing a major amount of polyethylene terephthalate, and metallic salts of terpene carboxylic acids to increase crystallization rates of crystalline resins. This publication, however, does not teach or suggest which of the metallic acids of terpene carboxylic acids can provide the thermoplastic resins with the best effect in the increase of crystallization rates, and the molded articles with the best mechanical and/or optical properties.

OBJECT OF THE INVENTION

In view of the prior art techniques as mentioned above, it is an object of the invention to provide a process for nucleating crystalline thermoplastic resins to accelerate or increase crystallization rates of the crystalline thermoplastic resins to improve mechanical properties and/or optical properties thereof. It is another object of the invention to provide a crystalline thermoplastic resin composition from which molded articles having improved mechanical and/or optical properties can be obtained.

SUMMARY OF THE INVENTION

We have now found that metallic salts of specific rosin acids can be used as a crystal nucleating agent for crystalline thermoplastic resins to yield superior results to those obtained with known crystal nucleating agents.

More particularly, in accordance with this invention, there is provided a crystalline thermoplastic resin composition containing a crystal nucleating agent comprising a metallic salt of rosin acid selected from the group consisting of those represented by the formula (Ia), formula (Ib), dihydropimaric acid and mixtures thereof:

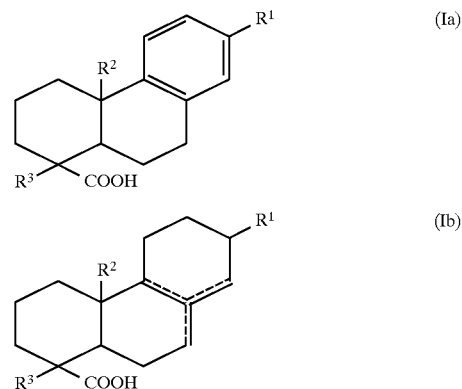

wherein each of $R^1$, $R^2$ and $R^3$, which may be the same or different, is independently a hydrogen atom, an alkyl group, a cycloalkyl group or an aryl group, and the three broken lines in the formula (Ib) represent possible positions for a chemical bond to form an unsaturated double bond, only one such double bond being present in formula (Ib). In formulae (Ia) and (Ib), preferably, $R^1$ is isopropyl, and each of $R^2$ and $R^3$ is methyl.

The metallic salt of the rosin acid is generally a monovalent to trivalent metallic salt, and may preferably be selected from sodium, potassium and magnesium salts.

In a preferred embodiment of the present invention, the metallic salt of the rosin acid comprises at least two metallic salts, in particular a combination of a potassium salt and a sodium salt, or of a sodium salt and a magnesium salt of the rosin acid. Further, the metallic salt of the rosin acid may comprise a free rosin acid.

The crystal nucleating agent of the invention is suitable for polyolefins, polyamides, polyesters and polyacetals.

The crystal nucleating agent according to the invention not only accelerates or increases crystallization rates of crystalline thermoplastic resins but also enables to form fine crystals of the resins. Therefore, from a crystalline thermoplastic resin containing this crystal nucleating agent, molded articles having excellent mechanical properties and/or optical properties can be obtained.

Thus, according to a first aspect of the present invention, there is provided a crystalline thermoplastic resin composition comprising:

(A) a crystalline thermoplastic resin, and (B) a crystallization rate increasing amount of a nucleating agent comprising a metallic salt of rosin acid selected from the group consisting of those represented by formula (Ia), formula (Ib), dihydropimaric acid and mixtures thereof:

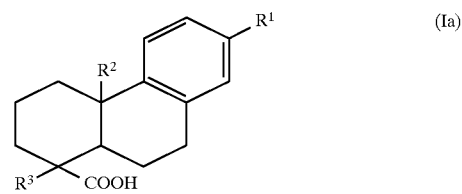

-continued

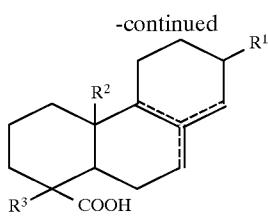

wherein each of R¹, R² and R³, which may be the same or different, is independently a hydrogen atom, an alkyl group, a cycloalkyl group or an aryl group, and the three broken lines in the formula (Ib) represent possible positions for a chemical bond to form an unsaturated double bond, only one such unsaturated double bond being present in formula (Ib).

This composition may optionally contain (C) a melt blending time decreasing effective amount of at least one compatibilizing agent selected from the group consisting of metallic salts of higher fatty acids, rosin glycerol esters, antistatic agents, polyolefin waxes and hydrogenated petroleum resins.

In a further aspect of the present invention there is provided a process for increasing the crystallization rate of a crystalline thermoplastic resin, the process comprising melt blending a crystallization rate increasing effective amount of a nucleating agent with a crystalline thermoplastic resin, wherein the nucleating agent comprises a metallic salt of a rosin acid selected from the group consisting of those represented by formula (Ia), formula (Ib), dihydropimaric acid and mixtures thereof:

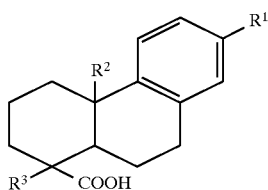

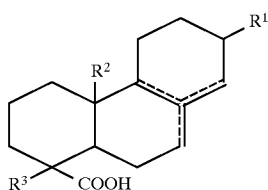

wherein each of R¹, R² and R³, which may be the same or different, is independently a hydrogen atom, an alkyl group, a cycloalkyl group or an aryl group, and the three broken lines in formula (Ib) represent possible positions for a chemical bond to form an unsaturated double bond, only one such unsaturated double bond being present in formula (Ib).

The process may further comprise the step of admixing a melt blending time decreasing effective amount of a compatibilizing agent with the nucleating agent and the crystalline thermoplastic resin prior to the melt blending, the compatibilizing agent being selected from the group consisting of higher fatty acid metallic salts, rosin glycerol esters, antistatic agents, polyolefin waxes and hydrogenated petroleum resins.

The crystalline thermoplastic resin (A) can be at least one selected from the group consisting of polyolefins, polyamides, polyesters and polyacetals.

The crystalline thermoplastic resin composition according to the present invention can crystallize at a high crystallization rate, and the molded articles formed therefrom have excellent mechanical properties and/or optical properties. It is a further advantage of the invention that the crystal nucleating agent can readily be dispersed in the crystalline thermoplastic resin for a short kneading time.

DETAILED DESCRIPTION OF THE INVENTION

Crystal nucleating agent for crystalline thermoplastic resins

The nucleating agent for crystalline thermoplastic resins according to the invention comprises a metallic salt of a rosin acid selected from the group consisting of those represented by formula (Ia), formula (Ib), dihydropimaric acid and mixtures thereof:

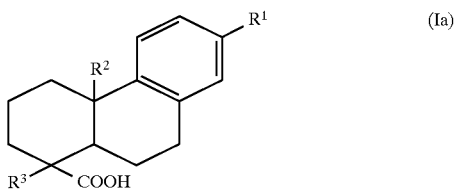

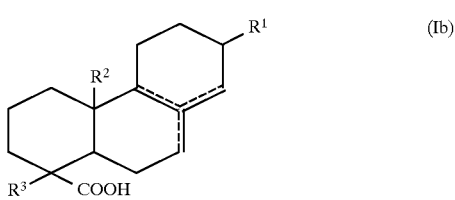

wherein each of R¹, R² and R³, which may be the same or different, is independently a hydrogen atom, an alkyl group, a cycloalkyl group or an aryl group, and the three broken lines in formula (Ib) represent possible positions for a chemical bond to form an unsaturated double bond, only one such unsaturated double bond being present in formula (Ib).

The term "a metallic salt of a rosin acid" or "a rosin acid metallic salt" used herein means a reaction product of a rosin acid with a metallic compound and includes single salts of one or more rosin acids, mixed salts of one or more rosin acids and two or more metals, and mixtures of the aforementioned salts with one or more free acids.

The salt content of the nucleating agent is usually 5 to 100 equivalent %, preferably 10 to 70 equivalent %, more preferably 20 to 50 equivalent %, based on the amount of the carboxyl group of the rosin acids.

The metallic compounds for forming the rosin acid metallic salts are those which have a metal such as sodium, potassium or magnesium, and are capable of reacting with the rosin acid. Examples of these compounds include chlorides, nitrates, acetates, sulfates, carbonates, oxides and hydroxides of the metal.

According to the invention, preferably the rosin acid is at least one selected from the compounds of the formulae (Ia) and (Ib):

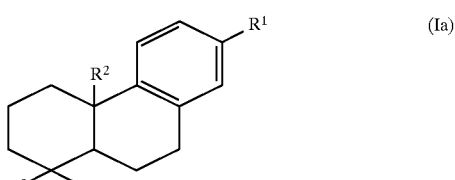

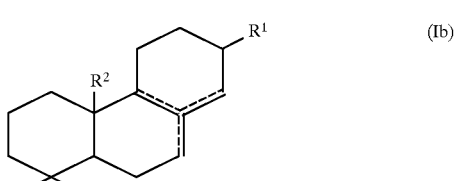

wherein each of R¹, R² and R³, which may be the same or different, is independently a hydrogen atom, an alkyl group, a cycloalkyl group or an aryl group, and the three broken lines in the formula (Ib) represent possible positions for a chemical bond to form an unsaturated double bond, only one such unsaturated double bond being present in formula (Ib).

The alkyl groups may have 1 to 8 carbon atoms, and are for example methyl, ethyl, n-propyl, i-propyl, n-butyl, i-butyl, tert-butyl, pentyl, heptyl and octyl. These groups may have substituents such as hydroxyl group, carboxyl group, alkoxy group (1 to 6 carbon atoms) and halogen atom.

The cycloalkyl groups may have 5 to 8 carbon atoms, and are for example cyclopentyl, cyclohexyl and cycloheptyl. These groups may have substituents such as hydroxyl group, carboxyl group, alkoxy group (1 to 6 carbon atoms) and halogen atom.

The aryl groups may have 6 to 10 carbon atoms, and are for example phenyl, tolyl and naphthyl. These groups may have substituents such as hydroxyl group, carboxyl group, alkoxy group (1 to 6 carbon atoms) and halogen atom.

Of the compounds (Ia) and (Ib), preferred are compounds in which $R^1$, $R^2$ and $R^3$ are identical or different alkyl groups, and more preferably $R^1$ is i-propyl, and $R^2$ and $R^3$ are each methyl, because the metallic salts of such compounds exhibit particularly improved effect in the crystallization rates of crystalline resins.

The compound (Ia) is typically represented by dehydroabietic acid, and the compound (Ib) is typically represented by a dihydroabietic acid.

For example, the compound of the formula (Ia) can be obtained by disproportionating or dehydrogenating natural rosins such as gum rosin, tall oil rosin or wood rosin and purifying it. The compound (Ib) can also be obtained by a similar procedure. The natural rosin generally contains two or more resin acids such as pimaric acid, sandarachpimaric acid, parastric acid, isopimaric acid, abietic acid, dehydroabietic acid, neoabietic acid, dihydropimaric acid, dihydroabietic acid and tetrahydroabietic acid.

The metallic salts of rosin acids of the formulae (Ia) and (Ib) may be represented by the following formulae (IIa) and (IIb), respectively:

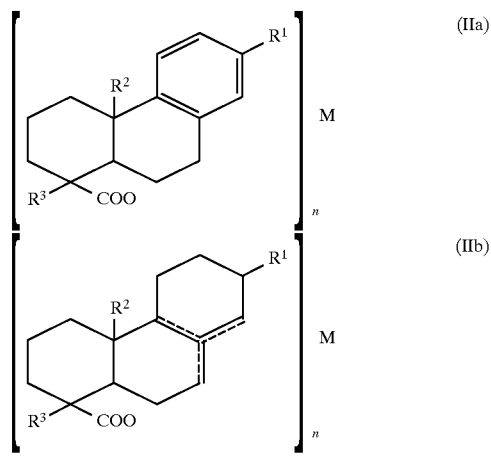

wherein $R^1$, $R^2$, $R^3$ and the three broken lines are as defined in the formulae (Ia) and (Ib), M is a monovalent to trivalent metallic ion, and n is an integer which is the same as the valence number of the metallic ion M, namely n is 1, 2 or 3.

Examples of M include monovalent metallic ions, such as lithium, sodium, potassium, rubidium and cesium; divalent metallic ions, such as beryllium, magnesium, calcium, strontium, barium and zinc; and trivalent metallic ions, such as aluminum. Preferably the metallic ions are monovalent and divalent metallic ions, particularly sodium ion, potassium ion and magnesium ion.

Preferably the compounds (IIa) and (IIb) are those in which $R^1$, $R^2$ and R3 are identical or different alkyl groups, or M is a monovalent or divalent metallic ion; more preferably $R^1$ is i-propyl, and $R^2$ and $R^3$ are each methyl, or M is sodium ion, potassium ion or magnesium ion. Particularly preferred are compounds (IIa) and (IIb) wherein $R^1$ is i-propyl, $R^2$ and $R^3$ are each methyl, and M is sodium ion, potassium ion or magnesium ion. Such compounds exhibit particularly improved effect in the crystallization rates of crystalline resins.

Examples of the compounds (IIa) include metallic salts of dehydroabietatic acid, such as lithium, sodium, potassium, beryllium, magnesium, calcium, zinc and aluminum salts of dehydroabietatic acid. Of these, preferred are sodium dehydroabietate, potassium dehydroabietate and magnesium dehydroabietate.

Examples of the compounds (IIb) include metallic salts of dihydroabietic acid, such as lithium, sodium, potassium, beryllium, magnesium, calcium, zinc and aluminum salts of dihydroabietatic acid. Of these, preferred are sodium dihydroabietate, potassium dihydroabietate and magnesium dihydroabietate.

The above-mentioned metallic salts of the rosin acid can be prepared by conventionally known methods including, for example, (1) a direct reaction method in which the reaction of a rosin acid with a metallic compound is directly carried out in the presence or absence of an organic solvent; and (2) a double decomposition method in which the exchange reaction takes place between a metallic salt of a rosin acid and a metallic compound in the presence of water and/or an organic solvent to produce a different metallic salt of the rosin acid.

In the direct reaction method (1), viewed from the point of view of yields and workability, it is preferable that the rosin acid is used in the form of a solution in the organic solvent and the metallic compound is then added to the solution to react them. Examples of the organic solvents usable herein include aromatic hydrocarbon solvents such as toluene and xylene; ester solvents such as ethyl acetate and butyl acetate; and ketone solvents such as methyl ethyl ketone and methyl isobutyl ketone. The organic solvent may be selected depending upon, for example, its solvency for the rosin acid and its easiness of separation from water in a working-up step.

The organic solvent may be used in an amount of usually about 20 to 250 parts by weight based on 100 parts by weight of the rosin acids, but not being limited thereto. The reaction temperature may be usually about 40° to 150° C., preferably 50° to 120° C., but not being limited thereto. The reaction of the rosin acid with the metallic compound is carried out so as to produce a metallic salt which contains the metal introduced in an amount of usually 5 to 100 equivalent %, preferably 10 to 70 equivalent %, more preferably 20 to 50 equivalent %, based on the amount of the carboxyl group of the rosin acid. After the end of the reaction, the reaction mixture is generally worked up in a conventional manner, for example, by distillation to remove the organic solvent. Although further work-up steps may be carried out to remove the unreacted metallic compound and the unreacted rosin acid to isolate the aimed metallic salt of rosin acid, the reaction product after distilling off the organic solvent can be directly used as a crystal nucleating agent according to the invention.

In the double decomposition method (2), viewed from the point of view of yields and workability, it is preferable that the metallic salt (e.g., alkaline metal salt) of the rosin acid dissolved in the organic solvent be reacted with a different metallic compound in the presence of water. The organic solvents as exemplified for the method (1) may also be used herein, and may be selected depending upon, for example, their solvency for the rosin acid and their easiness of separation from water in a working-up step.

The organic solvent may be used in an amount of usually about 100 to 1,000 parts by weight based on 100 parts by weight of the metallic salt of the rosin acid, but not being limited thereto. The reaction temperature may be usually about 40° to 150° C., preferably 50° to 90° C., but not being limited thereto. After the end of the reaction, the reaction mixture is generally worked up in a conventional manner, for example, by distillation to remove the organic solvent. Although further work-up steps may be carried out to remove the unreacted metallic compound and the unreacted metallic salt of rosin acid to isolate the aimed metallic salt of rosin acid, the reaction product after distilling off the organic solvent can be directly used as a crystal nucleating agent according to the invention.

The metallic salt of the rosin acid obtained as described above is preferably pulverized into fine particles for its use as a crystal nucleating agent so that its dispersibility in a crystalline thermoplastic resin can be improved and thus a homogeneous dispersion can be obtained.

For pulverizing the metallic salt of the rosin acid, conventionally known methods can be employed, for example, (a) the solid metallic salt of the rosin acid obtained is ground or milled by a wet or dry process, and (b) after the end of the reaction in the above method (1) or (2) as described, the reaction mixture in the form of a solution prior to the distillation of the organic solvent is emulsified or dispersed in water, optionally with the aid of a surface active agent and/or a water-soluble polymeric substance, and then the water and the organic solvent are distilled off.

In the above method (b), conventionally known surface active agents and/or water-soluble polymeric substances are usable, including, for example, nonionic surface active agents, anionic surface active agents, polyvinyl alcohol, alkali metal salts of poly(meth)acrylic acids, (meth)acrylic acid-acrylamide copolymers, water-soluble cellulose and starch. In the method (b), after the water and the organic solvent are distilled off, the resulting particulate metallic salt of the rosin acid may be washed with water to remove the surface active agent and/or water-soluble polymeric substance.

The above-mentioned metallic salts of rosin acids may be used singly or in combination as a crystal nucleating agent for crystalline thermoplastic resins. For example, combinations of two or more metallic salts are those comprising an identical rosin acid and different metals; different rosin acids and an identical metal; and different rosin acids and different metals. Among them, preferable combinations of at least two metallic salts are those comprising an identical rosin acid and at least two metals, particularly Ka and Na, or K+Mg.

As described above, a mixture of one or more metallic salts of one or more rosin acids can be used as a crystal nucleating agent, and such mixture may contain unreacted rosin acids. Preferably the crystal nucleating agent contains the metallic salt(s) in an amount of 5 to 100 equivalent %, more preferably 10 to 70 equivalent %, and particularly preferably 20 to 50 equivalent %, based on the amount of carboxyl group of the rosin acid.

The nucleating agents described above are used for accelerating the crystallization of various crystalline thermoplastic resins such as polyolefins, polyamides, polyesters and polyacetals.

The nucleating agents described above are used in an amount effective to increase the crystallization rate of the crystalline thermoplastic resin to which it is added. Typically, the nucleating agent is used in an amount of 0.001 to 5 parts by weight per 100 parts by weight of crystalline thermoplastic resin. Amounts less than 0.001 part by weight per 100 parts by weight of crystalline thermoplastic resin generally result in an insufficient increase in the crystallization rate. Amounts greater than 5 parts by weight per 100 parts by weight of crystalline thermoplastic resin generally produce no further increase in the crystallization rate and/or result in degradation of the resin properties.

Crystalline thermoplastic resin

As the crystalline thermoplastic resin, at least one crystalline thermoplastic resin selected from polyolefins, polyamides, polyesters and polyacetals may be used.

Examples of the polyolefins include olefin homopolymers, such as polyethylene, polypropylene, poly-1-butene, polymethylpentene and polymethylbutene; and olefin copolymers, such as a propylene-ethylene random copolymer. Of these, preferred are polyethylene, polypropylene and poly-1-butene. These polyolefins may be used singly or in combination. Particularly preferred are polymers and combinations comprising polypropylene as the major component.

Examples of the polyesters include aromatic polyesters, such as polyethylene terephthalate, polyethylene naphthalate and polybutylene terephthalate; polycaprolactone; and polyhydroxybutyrate. Of these, particularly preferred is polyethylene terephthalate. These polyesters may be used singly or in combination.

Examples of the polyamides include aliphatic polyamides, such as nylon-6, nylon-66, nylon-10, nylon-12 and nylon-46; and aromatic polyamides prepared from aromatic dicarboxylic acids and aliphatic diamines. Of these, particularly preferred is nylon-6. These polyamides may be used singly or in combination.

Examples of the polyacetals include polyformaldehyde (polyoxymethylene), polyacetaldehyde, polypropionaldehyde and polybutylaldehyde. Of these particularly preferred is polyformaldehyde. These polyacetals may be used singly or in combination.

Such crystalline thermoplastic resins as mentioned above may be used singly or in combination. In addition to these crystalline thermoplastic resins mentioned above, other crystalline thermoplastic resin may of course be used in combination.

Crystal nucleating agent

As the nucleating agent, the aforementioned crystal nucleating agent comprising a metallic salt of a rosin acid as its principal component, is used. More specifically, the rosin acid metallic salt preferably has at least one metal selected from the group consisting of sodium, potassium and magnesium.

Preferably the rosin acid is at least one selected from the group consisting of the compounds represented by the above formulae (Ia) and (Ib) wherein particularly preferably $R^1$ is isopropyl, and $R^2$ and $R^3$ are each methyl.

Thus, preferred crystal nucleating agent (B) is at least one salt selected from the group consisting of sodium salts, potassium salts and magnesium salts of one or more rosin acids of the formulae (Ia) and (Ib) as mentioned above.

In one preferred embodiment of the invention, at least two rosin acid metallic salts which comprise an identical rosin acid and at least two different metals; at least two different rosin acids and an identical metal; or at least two different rosin acids and at least two different metals, are used as the crystal nucleating agent. Further, partially neutralized rosin acid metallic salts (referred to as also rosin acid partial metallic salts), preferably having at least two metals, may be used. Thus, the crystal nucleating agent may contain 5 to 100 equivalent %, preferably 10 to 70 equivalent %, more preferably 20 to 50 equivalent %, based on the carboxyl group of the rosin acid(s).

When the rosin acid metallic salts contain at least two metals, it is desirable to combine these salts so that at least one salt amounts to 1 mol % or more, preferably 5 to 95 mol %, and the other at least one salt amounts to 99 mol % or less, preferably 95 to 5 mol %, based on the total amount of the salts, respectively.

Preferable combinations of at least two rosin acid partial metallic salts are those of a partial potassium salt with a partial sodium salt; and a partial potassium salt with a partial magnesium salt. In such combinations, it is desirable that the potassium salt amounts to 20 mol % or more, preferably 20 to 99 mol %, more preferably 40 to 95 mol %, particularly preferably 45 to 80 mol %, and sodium or magnesium salt amounts to 80 mol % or less, preferably 80 to 1 mol %, more preferably 60 to 5 mol %, particularly preferably 20 to 55 mol %, based on the total amount of the salts, respectively. These combinations of rosin acid partial metallic salts having at least two metals can be dispersed in crystalline thermoplastic resins more readily than those having one metal.

Compatibilizing agent

As the compatibilizing agent, higher fatty acid metallic salts, rosin glycerol esters, an antistatic agents, polyolefin waxes or hydrogenated petroleum resins can be used.

Examples of the higher fatty acid (i.e., $C_{12}$ and higher fatty acids, preferably $C_{12}$–$C_{22}$) metallic salts include magnesium stearate, magnesium laurate, magnesium palmitate, calcium stearate, calcium oleate, calcium laurate, barium stearate, barium oleate, barium laurate, barium arachidate, barium behenate, zinc stearate, zinc oleate, zinc laurate, lithium stearate, sodium stearate, sodium palmitate, sodium laurate, potassium stearate, potassium laurate, calcium 12-hydroxystearate and calcium montanate. Of these, preferred is calcium stearate. These higher fatty acid metallic salts may be used singly or in combination.

Examples of the rosin glycerol esters include glycerol esters of rosin acids as described above, and preferred are glycerol esters of purified disproportionated rosins. These rosin glycerol esters may be used singly or in combination.

Examples of the antistatic agents include:

glycerol fatty acid (i.e., $C_8$ and higher fatty acids, preferably $C_{12}$–$C_{22}$) esters, such as glycerol monolaurate, glycerol monomyristylate, glycerol monopalmitate, glycerol monostearate, glycerol monobehenate and glycerol monooleate;

diglycerol fatty acid esters, such as diglycerol monolaurate, diglycerol monomyristylate, diglycerol monopalmitate, diglycerol monostearate, diglycerol monobehenate and diglycerol monooleate;

sorbitan fatty acid esters, propylene glycol fatty acid esters, sucrose fatty acid esters, citric acid mono-, di- or tri-stearyl esters, pentaerythritol fatty acid esters, trimethylolpropane fatty acid esters, polyoxyethylene glycerol fatty acid esters, polyoxyethylene sorbitan fatty acid esters, polyethylene glycol fatty acid esters, polypropylene glycol fatty acid esters, polyoxyethylene glycol fatty acid alcohol ethers, polyoxyethylene alkylphenyl ethers, polyoxypropylene-polyoxyethylene block copolymers, polyethylene glycol, polypropylene glycol;

N,N-bis(2-hydroxyethyl)aliphatic (i.e., $C_8$ and higher, preferably $C_{12}$–$C_{22}$) amines, such as N,N-bis(2-hydroxyethyl)laurylamine, N,N-bis(2-hydroxyethyl)myristylamine, N,N-bis(2-hydroxyethyl)palmitylamine, N,N-bis(2-hydroxyethyl)stearylamine and N,N-bis(2-hydroxyethyl)oleylamine;

N,N-bis(2-hydroxyisopropyl)aliphatic amines, such as N,N-bis(2-hydroxyisopropyl)laurylamine, N,N-bis(2-hydroxyisopropyl)myristylamine, N,N-bis(2-hydroxyisopropyl)palmitylamine, N,N-bis(2-hydroxyisopropyl)stearylamine and N,N-bis(2-hydroxyisopropyl)oleylamine;

N,N-bis(2-hydroxyethyl)aliphatic amides, such as N,N-bis(2-hydroxyethyl)laurylamide, N,N-bis(2-hydroxyethyl)myristylamide, N,N-bis(2-hydroxyethyl)palmitylamide, N,N-bis(2-hydroxyethyl)stearylamide, N,N-bis(2-hydroxyethyl)behenylamide and N,N-bis(2-hydroxyethyl)oleylamide;

N,N-bis(2-hydroxyisopropyl)aliphatic amides, such as N,N-bis(2-hydroxyisopropyl)laurylamide, N,N-bis(2-hydroxyisopropyl)myristylamide, N,N-bis(2-hydroxyisopropyl)palmitylamide, N,N-bis(2-hydroxyisopropyl)stearylamide and N,N-bis(2-hydroxyisopropyl)oleylamide; and monoesters or diesters of the above-exemplified N,N-bis(2-hydroxyethyl)aliphatic amines and fatty acids such as lauric acid and stearic acid.

Of these, preferred are glycerol monolaurate, N,N-bis(2-hydroxyethyl(i.e., $C_2$ and higher, preferably $C_2$–$C_6$)) aliphatic amines and N,N-bis(2-hydroxyalkyl)aliphatic amides. These antistatic agents may be used singly or in combination.

Examples of the polyolefin waxes include polyethylene wax, polypropylene wax, oxidized polyethylene wax, acid-modified polyethylene wax and acid-modified polypropylene wax. These polyolefin waxes may be used singly or in combination.

Various known hydrogenated petroleum resins can be used, for example, hydrogenated products of aromatic hydrocarbon resins and hydrogenated products of terpene resins. Particular examples thereof include hydrogenated products of resins obtained by polymerizing at least one monomer selected from aromatic unsaturated hydrocarbons, for example, styrene, α-methylstyrene, vinyltoluene, vinylxylene, propenylbenzene, indene, methylindene and ethylindene, and terpenes. Also usable are hydrogenated products of resins obtained by polymerizing petroleum fractions (boiling point: 20° to 300° C., preferably 150° to 300° C.) which are by-products in cracking or reforming petroleum. These hydrogenated petroleum resins may be used singly or in combination.

These compatibilizing agents mentioned above can be used in combination, and it is preferred to use a higher fatty acid metallic salt in combination with other compatibilizing agent.

Most effective compatibilizing agents are higher fatty acid metallic salts, and among them, metallic stearates are most preferred.

The compatibilizing agents described above are used in an amount effective to decrease the melt blending time of the crystalline thermoplastic resin/nucleating agent composition to which it is added. Typically, the compatibilizing agent is used in an amount of 0.01 to 5 parts by weight per 100 parts by weight of crystalline thermoplastic resin. Amounts less than 0.01 part by weight per 100 parts by weight of crystalline thermoplastic resin generally result in an insufficient decrease in the melt blending time. Amounts greater than 5 parts by weight per 100 parts by weight of crystalline thermoplastic resin generally produce no further decrease in the melt blending time and/or result in degradation of the resin properties.

Crystalline thermoplastic resin composition

The crystalline thermoplastic resin composition of the invention comprises:

(A) a crystalline thermoplastic resin, and (B) a crystallization rate increasing effective amount of a nucleating agent as previously described (preferably, 0.001 to 5 parts by weight, more preferably 0.05 to 5 parts by weight, of nucleating agent per 100 parts by weight of crystalline thermoplastic resin).

The crystalline thermoplastic resin composition according to the invention has excellent properties inherent in the crystalline thermoplastic resin and can crystallize at a high crystallization rate. Further, from this composition, molded articles having excellent mechanical properties such as rigidity and thermal rigidity and/or optical properties such as transparency and glossiness can be obtained in economically advantageous manners.

In one preferred embodiment of the invention, the crystalline thermoplastic resin composition contains the crystal nucleating agent (B) which comprises a metallic salt of at least one rosin acid selected from those represented by the above formulae (Ia) and (Ib).

In a further preferred embodiment of the invention, the crystal nucleating agent (B) used comprises rosin acid metallic salts having at least two metals with or without unreacted (free) acids, because such nucleating agent can be dispersed in the crystalline thermoplastic resins for a short kneading time.

According to the invention, the crystalline thermoplastic resin composition may further contain the compatibilizing agent (C), as previously described, in an amount effective to decrease the melt blending time of the crystalline thermoplastic resin/nucleating composition to which it is added (preferably 0.01 to 5 parts by weight, more preferably 0.03 to 5 parts by weight, of the compatibilizing agent per 100 parts by weight of the resin). By the use of the compatibiling agent (C), the kneading time for obtaining homogeneous compositions may be shortened, and a combination of the compatibilizing agent (C) with rosin acid metallic salts having at least two metals as the nucleating agent (B) is particularly preferred.

Process

The crystalline thermoplastic resin composition of the invention can be prepared by conventionally known processes, for example, by melting and kneading the crystalline thermoplastic resin (A) together with the crystal nucleating agent (B) and optionally the compatibilizing agent (C) in, for example, an extruder or a kneader.

The crystalline thermoplastic resin composition of the invention may further contain various additives such as crosslinking agents, heat stabilizers, weathering stabilizers, lubricants, release agents, inorganic fillers, pigments, dyes and pigment dispersants with the proviso that the objects of the invention are not marred.

The crystalline thermoplastic resin composition of the invention can be favorably used as a molding material in a wide application field of from domestic to industrial articles, for example, food containers, electrical parts, electronic parts, automobile parts and mechanical parts.

EFFECT OF THE INVENTION

The nucleating agent for thermoplastic resins according to the invention accelerates crystallization rates of crystalline thermoplastic resins, as well as enabling the formation of fine crystals of the resins. From a crystalline thermoplastic resin containing this nucleating agent, molded articles having excellent mechanical properties and/or optical properties can be produced.

The crystalline thermoplastic resin composition according to the invention which comprises a crystalline thermoplastic resin such as polyolefin, polyamide, polyester or polyacetal, and a crystal nucleating agent according to the invention, and optionally, a compatibilizing agent, can crystallize at a high crystallization rate, and molded articles obtained therefrom have excellent mechanical properties and/or optical properties.

EXAMPLE

The present invention will be further described with reference to the following examples, but it should be construed that the invention is in no way limited to those examples.

Properties of crystalline thermoplastic resin compositions were evaluated by the following methods.

Crystallization rate: In a differential scanning calorimeter (DSC), pellets from a composition were melted and then cooled at a constant rate of 10° C./min. The crystallization rate of the composition was determined from the crystallization exothermic peak temperature [crystallization temperature (Tc)] measured by the DSC. The higher the crystallization temperature (Tc) rises, the faster is the crystallization rate.

Flexural modulus (FM): A compression molded sheet having a thickness of 2 mm was cut to give a specimen having a length of 100 mm, a width of 10 mm and a thickness of 2 mm. The flexural modulus (FM) was measured on the specimen in accordance with JIS K7203. The higher is the flexural modulus (FM), the higher is the rigidity.

Transparency (haze): The haze was measured on a compression molded specimen having a thickness of 1.0 mm in accordance with JIS K6714. The lower is the haze, the higher is the transparency.

Examples 1–9

To 100 parts by weight of a homopolypropylene (MFR measured at 230° C. under a load of 2.16 kg: 1.2 g/10 min) were added 0.1 part by weight of Irganox 1010™ (available from Ciba-Geigy Co.) and 0.1 part by weight of calcium stearate, and was further added one of the crystal nucleating agents set forth in Table 1 in each amount set forth in Table 2, respectively. The resulting mixture was melt blended in an extruder at a resin temperature of 230° C., followed by pelletizing.

The pellets thus obtained were subjected to compression and injection molding at a melt temperature of 230° C. and a cooling temperature of 20° C. to prepare specimens, on which properties were measured by the aforementioned test methods. The results are set forth in Table 2.

TABLE 1

| Crystal nucleating agent | Rosin acid Structure | Purity*1 | Salt Metal | Salt content*2 |
|---|---|---|---|---|
| A | (dehydroabietic acid structure: tricyclic with CH₃ groups, CH(CH₃)₂, COOH) | 100 | Mg | 35 |
| B | " | 81 | Mg | 35 |
| C | " | 81 | Na | 35 |
| D | " | 81 | K | 35 |
| E | " | 61 | Mg | 35 |
| F | (abietic acid type structure with double bonds, CH₃ groups, CH(CH₃)₂, COOH) | 58 | Mg | 35 |

*1: % by weight.
*2: % equivalent of metal to carboxyl group.

Comparative Example 1

Pellets were prepared in the same manner as described in Examples 1 to 9 except that no crystal nucleating agent was used.

Specimens were prepared from the pellets and measured for properties as described above. The results are set forth in Table 2.

Comparative Example 2

Pellets were prepared in the same manner as described in Examples 1 to 9 except that the crystal nucleating agent was replaced by 0.3 part by weight of aluminum para-t-butylbenzoate (trade name: ALPTBB™, available from Shell Chemical Co.) (compound G).

Specimens were prepared from the pellets and measured for properties as described above. The results are set forth in Table 2.

Comparative Example 3

Pellets were prepared in the same manner as described in Examples 1 to 9 except that the crystal nucleating agent was replaced by 0.3 part by weight of dibenzylidene sorbitol (trade name: EC-1™, available from E.C. Kagaku K.K.) (compound H).

Specimens were prepared from the pellets and measured for properties as described above. The results are set forth in Table 2.

TABLE 2

| | Crystal nucleating agent | Amount* | Tc (°C.) | FM (kgf/cm²) | Haze (%) |
|---|---|---|---|---|---|
| Ex. 1 | A | 0.3 | 128 | 20,300 | 35 |
| Ex. 2 | B | 0.3 | 126 | 20,200 | 40 |
| Ex. 3 | C | 0.3 | 122 | 19,500 | 45 |
| Ex. 4 | D | 0.3 | 125 | 20,100 | 42 |
| Ex. 5 | B | 0.9 | 129 | 21,200 | 30 |
| Ex. 6 | C | 0.9 | 124 | 20,500 | 40 |
| Ex. 7 | D | 0.9 | 128 | 21,000 | 33 |
| Ex. 8 | E | 0.3 | 123 | 19,800 | 41 |
| Ex. 9 | F | 0.3 | 123 | 19,900 | 40 |
| Comp. Ex. 1 | none | — | 110 | 16,800 | 57 |
| Comp. Ex. 2 | G | 0.3 | 122 | 19,200 | 50 |
| Comp. Ex. 3 | H | 0.3 | 118 | 17,400 | 45 |

*Part by weight

Examples 10–18

To 100 parts by weight of a linear low-density polyethylene (MFR measured at 190° C. under a load of 2.16 kg: 2.3 g/10 min, density at 23° C.: 0.920 g/cc) were added 0.1 part by weight of Irganox 1076™ (available from Ciba-Geigy Co.) and 0.1 part by weight of calcium stearate, and was further added one of the crystal nucleating agents set forth in Table 1 in each amount set forth in Table 3, respectively. The resulting mixture was melt blended in an extruder at a resin temperature of 200° C., followed by pelletizing.

The pellets thus obtained were subjected to compression molding at a melt temperature of 200° C. and a cooling temperature of 20° C. to prepare specimens on which properties were measured by the aforementioned test methods. The results are set forth in Table 3.

Comparative Example 4

Pellets were prepared in the same manner as described in Examples 10 to 18 except that no crystal nucleating agent was used.

Specimens were prepared from the pellets and measured for properties as described above. The results are set forth in Table 3.

Comparative Example 5

Pellets were prepared in the same manner as described in Examples 10 to 18 except that 0.3 part by weight of the compound H was used as the crystal nucleating agent.

Specimens were prepared from the pellets and measured for properties as described above. The results are set forth in Table 3.

TABLE 3

| | Crystal nucleating agent | Amount* | Tc (°C.) | FM (kgf/cm$^2$) | Haze (%) |
|---|---|---|---|---|---|
| Ex. 10 | A | 0.3 | 104 | 33,500 | 60 |
| Ex. 11 | B | 0.3 | 103 | 32,200 | 65 |
| Ex. 12 | C | 0.3 | 103 | 32,600 | 62 |
| Ex. 13 | D | 0.3 | 103 | 32,500 | 64 |
| Ex. 14 | B | 0.9 | 105 | 35,700 | 58 |
| Ex. 15 | C | 0.9 | 105 | 35,300 | 52 |
| Ex. 16 | D | 0.9 | 105 | 35,200 | 55 |
| Ex. 17 | E | 0.3 | 103 | 32,300 | 62 |
| Ex. 18 | F | 0.3 | 103 | 32,600 | 63 |
| Comp. Ex. 4 | none | — | 100 | 30,200 | 84 |
| Comp. Ex. 4 | H | 0.3 | 102 | 31,000 | 72 |

*Part by weight.

Examples 19–25

To 100 parts by weight of a nylon-6 resin (trade name: Amilan CM 1021, available from Toray Industries, Inc.) was added one of the nucleating agents set forth in Table 1 in each amount set forth in Table 4, respectively. The resulting mixture was melt blended in an extruder at a resin temperature of 280° C., followed by pelletizing.

The pellets thus obtained were subjected to compression molding at a melt temperature of 280° C. and a cooling temperature of 20° C. to prepare specimens, on which properties were measured by the above-mentioned test methods. The results are set forth in Table 4.

Comparative Example 6

Pellets were prepared in the same manner as described in Examples 19 to 25 except that no crystal nucleating agent was used.

Specimens were prepared from the pellets and measured for properties as described above. The results are set forth in Table 4.

TABLE 4

| | Crystal nucleating agent | Amount* | Tc (°C.) | FM (kgf/cm$^2$) |
|---|---|---|---|---|
| Ex. 19 | A | 0.3 | 196 | 32,100 |
| Ex. 20 | B | 0.3 | 195 | 31,800 |
| Ex. 21 | C | 0.3 | 201 | 33,000 |
| Ex. 22 | D | 0.3 | 202 | 33,200 |
| Ex. 23 | E | 0.3 | 200 | 32,800 |
| Ex. 24 | F | 0.3 | 199 | 32,600 |
| Ex. 25 | C | 0.9 | 205 | 34,000 |
| Comp. Ex. 6 | none | — | 191 | 28,700 |

*Part by weight.

Examples 26–32

To 100 parts by weight of a polyethylene terephthalate resin (trade name: J125, available from Mitsui PET Resin K.K.) was added one of the nucleating agents set forth in Table 1 or Table 5 in each amount set forth in Table 6, respectively. The resulting mixture was melt blended in an extruder at a resin temperature of 280° C., followed by pelletizing.

The pellets thus obtained were subjected to compression molding at a melt temperature of 280° C. and a cooling temperature of 20° C. to prepare specimens, on which properties were measured by the aforementioned test methods. The results are set forth in Table 6.

Comparative Example 7

Pellets were prepared in the same manner as described in Examples 26 to 32 except that no crystal nucleating agent was used.

Specimens were prepared from the pellets and measured for properties as described above. The results are set forth in Table 6.

Comparative Example 8

Pellets were prepared in the same manner as described in Examples 26 to 32 except that 0.3 part by weight of the crystal nucleating agent K set forth in Table 5 was used.

Specimens were prepared from the pellets and measured for properties as described above. The results are set forth in Table 6.

TABLE 5

| Crystal nucleating agent | Rosin acid | | Salt Metal | Salt content*2 |
|---|---|---|---|---|
| | Structure | Purity*1 | | |
| I | 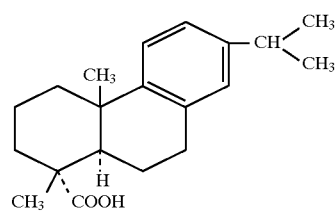 | 61 | Na | 35 |

TABLE 5-continued

| Crystal nucleating agent | Rosin acid Structure | Purity*1 | Salt Metal | Salt content*2 |
|---|---|---|---|---|
| J | (structure) | 81 | Na | 35 |
| K | (structure) | 80 | Mg | 35 |

*1: % by weight.
*2: % equivalent of metal to carboxyl group.

TABLE 6

| | Crystal nucleating agent | Amount* | Tc (°C.) | FM (kgf/cm²) |
|---|---|---|---|---|
| Ex. 26 | A | 0.3 | 199 | 36,500 |
| Ex. 27 | B | 0.3 | 197 | 36,000 |
| Ex. 28 | C | 0.3 | 209 | 40,000 |
| Ex. 29 | D | 0.3 | 211 | 40,600 |
| Ex. 30 | I | 0.3 | 208 | 39,800 |
| Ex. 31 | C | 0.9 | 218 | 41,600 |
| Ex. 32 | J | 0.3 | 208 | 39,700 |
| Comp. Ex. 7 | none | — | 192 | 31,500 |
| Comp. Ex. 8 | K | 0.3 | 193 | 32,000 |

*% by weight.

Examples 33–40

To 100 parts by weight of a propylene-ethylene random copolymer (MFR measured at 230° C. under a load of 2.16 kg: 19 g/10 min) were added 0.15 part by weight of Irgaphos 168™ (available from Ciba-Geigy Co.) and 0.1 part by weight of calcium stearate, and was further added each of the following crystal nucleating agents set forth in Table 7 in each amount set forth in Table 8, respectively. The resulting mixture was melt blended in a 20 mm single screw extruder at a resin temperature of 220° C., followed by pelletizing.

The pellets thus obtained were subjected to compression molding at a melt temperature of 230° C. and a cooling temperature of 20° C. to prepare specimens, on which properties were measured by the aforementioned test methods. The results are set forth in Table 8.

TABLE 7

(structure)

| Crystal nucleating agent | % Equivalent of meal to carboxyl group | | |
|---|---|---|---|
| | K | Na | Mg |
| L | 28.5 | 1.5 | — |
| M | 27 | 3 | — |
| N | 24 | 6 | — |
| O | 21 | 9 | — |
| P | 15 | 15 | — |
| Q | 28.5 | — | 1.5 |
| R | 27 | — | 3 |
| S | — | 10 | 30 |
| T | 36 | 4 | — |
| U | 32 | 8 | — |
| V | 30 | — | — |
| W | 20 | — | — |

Examples 41 & 42

To 100 parts by weight of a propylene-ethylene random copolymer (MFR measured at 230° C. under a load of 2.16 kg: 19 g/10 min) were added 0.15 part by weight of Irgaphos 168™ (available from Ciba-Geigy Co.) and 0.1 part by weight of calcium stearate, and were further added 0.45 part by weight of the crystal nucleating agent T or U and 0.15 part by weight of a rosin glycerol ester. The resulting mixture was melt blended in a 20 mm single screw extruder at a resin temperature of 220° C., followed by pelletizing.

Specimens were prepared from the pellets and measured for properties by the aforementioned test methods. The results are set forth in Table 8.

19

Comparative Example 9

Pellets were prepared in the same manner as described in Examples 33 to 40 except that no crystal nucleating agent was used.

Specimens were prepared from the pellets and measured for properties by the aforementioned test methods. The results are set forth in Table 8.

Example 43

Pellets were prepared in the same manner as described in Examples 33 to 40 except that 0.6 part by weight of the crystal nucleating agent W was used.

Specimens were prepared from the pellets and measured for properties by the aforementioned test methods. The results are set forth in Table 8.

20 mixture was melt blended in a 20 mm single screw extruder at a resin temperature of 220° C., followed by pelletizing.

Specimens were prepared from the pellets and measured for properties by the aforementioned test methods. The results are set forth in Table 9.

Examples 54–57

To 100 parts by weight of a propylene-ethylene random copolymer (MFR measured at 230° C. under a load of 2.16 kg: 19 g/10 min) were added 0.15 part by weight of Irgaphos 168™ (available from Ciba-Geigy Co.) and 0.1 part by weight of calcium stearate, and were further added one of the crystal nucleating agents set forth in Table 7 and one of the following antistatic agents (compatibilizing agents c-1 to c-4) in each amount set forth in Table 9, respectively. The resulting mixture was melt blended in a 20 mm single screw extruder at a resin temperature of 220° C., followed by pelletizing.

TABLE 8

| | Crystal nucleating agent | Amount*1 | Properties of molded article*2 | | | Properties of molded article*3 | | |
|---|---|---|---|---|---|---|---|---|
| | | | Haze (%) | Tc (°C.) | FM (kg/cm²) | Haze (%) | Tc (°C.) | FM (kg/cm²) |
| Ex. 32 | M | 0.6 | 31 | 113 | 12,200 | 22 | 115 | 12,400 |
| Ex. 33 | N | 0.6 | 34 | 113 | 12,100 | 22 | 114 | 12,000 |
| Ex. 34 | O | 0.6 | 22 | 113 | 12,900 | 18 | 115 | 13,100 |
| Ex. 35 | P | 0.6 | 22 | 113 | 13,200 | 18 | 115 | 13,100 |
| Ex. 36 | Q | 0.6 | 21 | 115 | 12,900 | 13 | 116 | 13,400 |
| Ex. 37 | R | 0.6 | 36 | 113 | 12,200 | 27 | 115 | 12,200 |
| Ex. 38 | S | 0.6 | 38 | 114 | 12,000 | 26 | 115 | 12,300 |
| Ex. 39 | T | 0.6 | 56 | 112 | 11,800 | 32 | 114 | 12,500 |
| Ex. 40 | U | 0.45 | 25 | 111 | 12,900 | 22 | 114 | 13,300 |
| Ex. 41 | V | 0.45 | 26 | 111 | 12,700 | 22 | 115 | 13,300 |
| Comp. Ex. 9 | — | 0 | 59 | 98 | 10,700 | 65 | 99 | 10,800 |
| Ex. 43 | W | 0.6 | 38 | 114 | 12,900 | 22 | 117 | 13,400 |

*1: Part by weight
*2: The melt blending operation was carried out once.
*3: The melt blending operation was carried out twice.

Examples 44–46

To 100 parts by weight of a propylene-ethylene random copolymer (MFR measured at 230° C. under a load of 2.16 kg: 19 g/10 min) was added 0.15 part by weight of Irgaphos 168™ (available from Ciba-Geigy Co.), and were further added one of the crystal nucleating agents set forth in Table 7 and calcium stearate (compatibilizing agent a) in each amount set forth in Table 9, respectively. The resulting mixture was melt blended in a 20 mm single screw extruder at a resin temperature of 220° C., followed by pelletizing.

The pellets thus obtained were subjected to compression molding at a melt temperature of 230° C. and a cooling temperature of 20° C. to prepare specimens, on which properties were measured by the aforementioned test methods. The results are set forth in Table 9.

Examples 47–53

To 100 parts by weight of a propylene-ethylene random copolymer (MFR measured at 230° C. under a load of 2.16 kg: 19 g/10 min) were added 0.15 part by weight of Irgaphos 168™ (available from Ciba-Geigy Co.) and 0.1 part by weight of calcium stearate, and were further added one of the crystal nucleating agents set forth in Table 7 and a rosin glycerol ester (trade name: KE-100, available from Arakawa Chemical Industries, Ltd.) (compatibilizing agent b) in each amount set forth in Table 9, respectively. The resulting Specimens were prepared from the pellets obtained and measured for properties by the aforementioned test methods. The results are set forth in Table 9.

| Compatibilizing agent | |
|---|---|
| C-1 | Electreostripper TS-2 ™ (Kao Co., Ltd.) |
| C-2 | Electreostripper TS-5 ™ (Kao Co., Ltd.) |
| C-3 | Chemistat 4700 ™ (Sanyo Chemical Industries, Ltd.) |
| C-4 | Dusper LA2000 ™ (Miyoshi Oil & Fat Co., Ltd.) |

Example 58

To 100 parts by weight of a propylene-ethylene random copolymer (MFR measured at 230° C. under a load of 2.16 kg: 19 g/10 min) were added 0.15 part by weight of Irgaphos 168™ (available from Ciba-Geigy Co.) and 0.1 part by weight of calcium stearate, and were further added one of the crystal nucleating agents set forth in Table 7 and a hydrogenated petroleum resin (trade name: Arkon P-140, available from Arakawa Chemical Industries, Ltd..) (compatibilizing agent d) in each amount set forth in Table 10, respectively. The resulting mixture was melt blended in a 20 mm single screw extruder at a resin temperature of 220° C., followed by pelletizing.

Specimens were prepared from the pellets obtained and measured for properties by the aforementioned test methods. The results are set forth in Table 10.

Examples 59–63

To 100 parts by weight of a propylene-ethylene random copolymer (MFR measured at 230° C. under a load of 2.16 kg: 19 g/10 min) were added 0.15 part by weight of Irgaphos 168™ (available from Ciba-Geigy Co.) and 0.1 part by weight of calcium stearate, and were further added one of the crystal nucleating agents set forth in Table 7 and one of the following polyolefin waxes (compatibilizing agents e-1 to e-4) in the amounts set forth in Table 10, respectively. The resulting mixture was melt blended in a 20 mm single screw extruder at a resin temperature of 220° C., followed by pelletizing.

Specimens were prepared from the pellets obtained and measured for properties by the aforementioned test methods. The results are set forth in Table 10.

| Compatibilizing agent | |
|---|---|
| e-1 | Polypropylene wax NP055 |
| e-2 | Oxidized polyethylene wax 4202E |
| e-3 | Acid-modified polyethylene wax 1105A |
| e-4 | Acid-modified polypropylene wax NP0555 |

(All available from Mitsui Petrochemical Industries, Ltd.)

Comparative Example 10

Pellets were prepared in the same manner as described in Examples 44 to 46 except that no crystal nucleating agent was used.

Specimens were prepared from the pellets obtained and measured for properties by the aforementioned test methods. The results are set forth in Table 10.

TABLE 9

| | Crystal nucleating agent | Amount*1 | Compatibilizing agent | Amount *1 |
|---|---|---|---|---|
| Ex. 44 | W | 0.6 | a | 0.03 |
| Ex. 45 | W | 0.6 | a | 0.05 |
| Ex. 46 | W | 0.6 | a | 0.1 |
| Ex. 47 | V | 0.4 | b | 0.2 |
| Ex. 48 | W | 0.45 | b | 0.15 |
| Ex. 49 | W | 0.6 | b | 0.2 |
| Ex. 50 | V | 0.3 | b | 0.3 |
| Ex. 51 | V | 0.6 | b | 0.6 |
| Ex. 52 | T | 0.45 | b | 0.15 |
| Ex. 53 | U | 0.45 | b | 0.15 |
| Ex. 54 | W | 0.6 | c-1 | 0.3 |
| Ex. 55 | W | 0.6 | c-2 | 0.3 |
| Ex. 56 | W | 0.6 | c-3 | 0.3 |
| Ex. 57 | W | 0.6 | c-4 | 0.3 |
| Comp. Ex. 10 | — | 0 | a | 0.1 |

| | Properties of molded article *2 | | | Properties of molded article *3 | | |
|---|---|---|---|---|---|---|
| | Haze (%) | Tc (°C.) | FM (kg/cm$^2$) | Haze (%) | Tc (°C.) | FM (kg/cm$^2$) |
| Ex. 44 | 35 | 114 | 12,000 | 31 | 116 | 12,100 |
| Ex. 45 | 39 | 115 | 11,800 | 29 | 116 | 12,400 |
| Ex. 46 | 39 | 114 | 11,900 | 27 | 115 | 12,400 |
| Ex. 47 | 35 | 113 | 12,000 | 23 | 114 | 12,100 |

TABLE 9-continued

| Ex. 48 | 41 | 113 | 12,200 | 29 | 115 | 12,100 |
|---|---|---|---|---|---|---|
| Ex. 49 | 26 | 116 | 12,400 | 24 | 117 | 13,000 |
| Ex. 50 | 67 | 113 | 11,500 | 39 | 114 | 12,200 |
| Ex. 51 | 26 | 116 | 12,500 | 23 | 117 | 12,800 |
| Ex. 52 | 21 | 113 | 12,900 | 13 | 116 | 13,300 |
| Ex. 53 | 22 | 113 | 12,700 | 12 | 116 | 13,300 |
| Ex. 54 | 33 | 115 | 11,900 | 22 | 116 | 12,300 |
| Ex. 55 | 38 | 115 | 11,600 | 26 | 115 | 12,400 |
| Ex. 56 | 41 | 113 | 11,700 | 21 | 115 | 12,400 |
| Ex. 57 | 30 | 115 | 12,200 | 18 | 116 | 12,600 |
| Comp. Ex. 10 | 59 | 98 | 10,700 | 65 | 99 | 10,800 |

*1: Part by weight.
*2: The melt blending operation was carried out once.
*3: The melt blending operation was carried out twice.

TABLE 10

| | Crystal nucleating agent | Amount*1 | Compatibilizing agent | Amount *1 |
|---|---|---|---|---|
| Ex. 58 | V | 0.4 | d | 0.2 |
| Ex. 59 | W | 0.55 | e-1 | 0.05 |
| Ex. 60 | W | 0.45 | e-1 | 0.15 |
| Ex. 61 | W | 0.45 | e-2 | 0.15 |
| Ex. 62 | W | 0.45 | e-3 | 0.15 |
| Ex. 63 | W | 0.45 | e-4 | 0.15 |

| | Properties of molded article *2 | | | Properties of molded article *3 | | |
|---|---|---|---|---|---|---|
| | Haze (%) | Tc (°C.) | FM (kg/cm$^2$) | Haze (%) | Tc (°C.) | FM (kg/cm$^2$) |
| Ex. 58 | 62 | 105 | 11,500 | 39 | 113 | 12,200 |
| Ex. 59 | 38 | 114 | 12,300 | 28 | 116 | 12,300 |
| Ex. 60 | 45 | 113 | 11,600 | 34 | 115 | 11,900 |
| Ex. 61 | 46 | 114 | 12,600 | 32 | 114 | 12,300 |
| Ex. 62 | 57 | 111 | 11,900 | 37 | 114 | 11,900 |
| Ex. 63 | 68 | 105 | 11,400 | 63 | 111 | 12,300 |

*1: Part by weight.
*2: The melt blending operation was carried out once.
*3: The melt blending operation was carried out twice.

What is claimed is:

1. A process for increasing the crystallization rate of crystalline thermoplastic resin, the process consisting of:

melt blending a crystallization rate increasing effective amount of a nucleating agent with crystalline thermoplastic resin;

wherein said nucleating agent consists of (i) at least one metallic salt of rosin acid selected from the group consisting of those represented by the formula (Ia), formula (Ib), dihydropimaric acid and mixtures thereof:

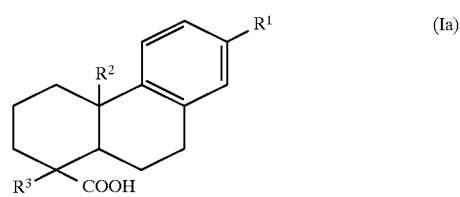

(Ia)

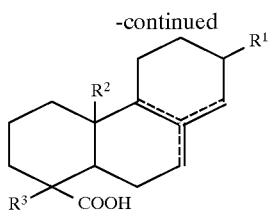

wherein each of $R^1$, $R^2$ and $R^3$, which may be the same or different, is independently a hydrogen atom, an alkyl group, a cycloalkyl group or an aryl group, and the three broken lines in formula (Ib) represent possible positions for a chemical bond to form an unsaturated double bond, only one such unsaturated double bond being present in formula (Ib) and (ii) at least one free acid selected from the group consisting of those represented by formula (Ia), formula (Ib), dihydropimaric acid and mixtures thereof, wherein said at least one metallic salt is 5 to 100 equivalent % of said nucleating agent, based on the total amount of the carboxyl groups of rosin acid and wherein said at least one metallic salt is selected from the group consisting of potassium salt, sodium salt, magnesium salt and mixtures thereof; and wherein said crystalline thermoplastic resin is selected from the group consisting of polyolefins, polyamides, polyesters, polyacetals, mixtures thereof and mixtures of one or more thereof with one or more additives selected from the group consisting of crosslinking agents, heat stabilizers, weathering stabilizers, lubricants, release agents, inorganic fillers, pigments, dyes and pigment dispersants.

2. The process as claimed in claim 1, wherein said rosin acid is selected from the group consisting of dehydroabietic acid, dihydroabietic acid and dihydropimaric acid.

3. The process as claimed in claim 1, wherein $R^1$ is isopropyl and $R^2$ and $R^3$ are each methyl.

4. The process as claimed in claim 1, wherein said at least one metallic salt is a mixture of a potassium salt and a sodium salt or a mixture of a potassium salt and a magnesium salt.

5. The process as claimed in claim 4, wherein said potassium salt is 40 to 95 mol %, based on the total salt content, and said sodium salt or said magnesium salt is 60 to 5 mol %, based on the total salt content.

6. The process as claimed in claim 1, wherein said at least one metallic salt is 20 to 50 equivalent % of said nucleating agent, based on the total amount of the carboxyl groups of rosin acid.

7. The process as claimed in claim 1, wherein said nucleating agent is utilized in an amount of 0.001 to 5 parts by weight per 100 parts by weight of crystalline thermoplastic resin.

8. A process for increasing the crystallization rate of crystalline thermoplastic resin, the process consisting of:

admixing a melt blending time decreasing effective amount of compatibilizing agent, a crystallization rate increasing effective amount of a nucleating agent and crystalline thermoplastic resin; and melt blending said admixture of a melt blending time decreasing effective amount of compatibilizing agent, a crystallization rate increasing effective amount of a nucleating agent and crystalline thermoplastic resin;

wherein said compatibilizing agent is at least one member selected from the group consisting of $C_{12}$–$C_{22}$ higher fatty acid metallic salts, rosin glycerol ethers, antistatic agents, polyolefin waxes and hydrogenated petroleum resins;

wherein said nucleating agent consists of (i) at least one metallic salt of rosin acid selected from the group consisting of those represented by the formula (Ia), formula (Ib), dihydropimaric acid and mixtures thereof:

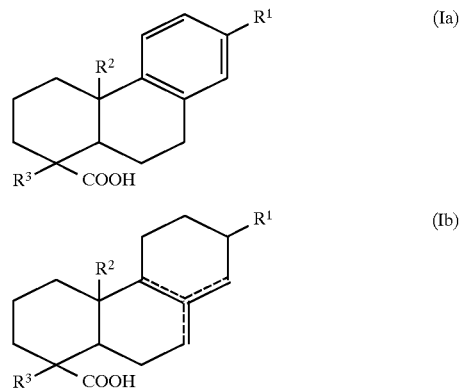

wherein each of $R^1$, $R^2$ and $R^3$, which may be the same or different, is independently a hydrogen atom, an alkyl group, a cycloalkyl group or an aryl group, and the three broken lines in formula (Ib) represent possible positions for a chemical bond to form an unsaturated double bond, only one such unsaturated double bond being present in formula (Ib) and (ii) at least one free acid selected from the group consisting of those represented by formula (Ia), formula (Ib), dihydropimaric acid and mixtures thereof, wherein said at least one metallic salt is 5 to 100 equivalent % of said nucleating agent, based on the total amount of the carboxyl groups of rosin acid; and wherein said at least one metallic salt is selected from the group consisting of potassium salt, sodium salt, magnesium salt and mixtures thereof and wherein said crystalline thermoplastic resin is selected from the group consisting of polyolefins, polyamides, polyesters, polyacetals, mixtures thereof and mixtures of one or more thereof with one or more additives selected from the group consisting of crosslinking agents, heat stabilizers, weathering stabilizers, lubricants, release agents, inorganic fillers, pigments, dyes and pigment dispersants.

9. The process as claimed in claim 8, wherein said rosin acid is selected from the group consisting of dehydroabietic acid, dihydroabietic abietic acid and dihydropimaric acid.

10. The process as claimed in claim 8, wherein $R^1$ is isopropyl and $R^2$ and $R^3$ are each methyl.

11. The process as claimed in claim 8, wherein said at least one metallic salt is a mixture of a potassium salt and a sodium salt or a mixture of a potassium salt and a magnesium salt.

12. The process as claimed in claim 11, wherein said potassium salt is 40 to 95 mole %, based on the total salt content, and said sodium salt or said magnesium salt is 60 to 5 mol %, based on the total salt content.

13. The process as claimed in claim 8, wherein said at least one metallic salt is 20 to 50 equivalent % of said nucleating agent, based on the total amount of the carboxyl groups of rosin acid.

14. The process as claimed in claim 8, wherein said nucleating agent is utilized in an amount of 0.001 to 5 parts by weight per 100 parts by weight of crystalline thermoplastic resin.

15. The process as claimed in claim 8, wherein said compatibility agent is utilized in an amount of 0.01 to 5 parts by weight per 100 parts by weight of crystalline thermoplastic resin.

* * * * *